United States Patent [19]
Munny

[11] Patent Number: 5,342,289
[45] Date of Patent: Aug. 30, 1994

[54] HYPEREXTENSION ORTHESIS WITH MOVABLE FRONT PAD

[76] Inventor: Kurt Munny, Hauptstrasse 239, D-5060 Bergisch Gladbach 2, Fed. Rep. of Germany

[21] Appl. No.: 829,064
[22] PCT Filed: Aug. 27, 1990
[86] PCT No.: PCT/EP90/01428
§ 371 Date: Jun. 10, 1992
§ 102(e) Date: Jun. 10, 1992
[87] PCT Pub. No.: WO91/03216
PCT Pub. Date: Mar. 21, 1991

[30] Foreign Application Priority Data
Aug. 30, 1989 [DE] Fed. Rep. of Germany ....... 3928628

[51] Int. Cl.$^5$ .................. A61F 5/00; A61F 5/24; A61F 5/28
[52] U.S. Cl. .................. 602/19; 128/99.1; 128/106.1
[58] Field of Search .......... 128/876, 95.1, 96.1, 128/99.1, 106.1, 108.1, DIG. 19; 602/19

[56] References Cited

U.S. PATENT DOCUMENTS

| | | |
|---|---|---|
| 31,564 | 4/1984 | Hendricks . |
| 2,808,050 | 10/1957 | Ward . |
| 3,945,376 | 3/1976 | Kuehnegger . |
| 3,945,376 | 3/1976 | Kuehnegger .......... 602/19 |
| 4,173,973 | 11/1979 | Hendrick .......... 602/19 |
| 4,640,269 | 2/1987 | Goins .......... 602/19 |
| 4,829,989 | 5/1989 | Deamer et al. .......... 602/19 |
| 4,976,257 | 12/1990 | Akin .......... 602/19 |
| 5,086,757 | 2/1992 | Lestini .......... 602/19 |
| 5,135,471 | 8/1992 | Houswerth .......... 602/19 |
| 5,176,622 | 1/1993 | Anderson .......... 602/19 |

OTHER PUBLICATIONS

Journal Medizinisch-Orthopadische Technik, 1987, pp. 711-712, "Otto Bock Hyperextensionsorthese in Modularbauweise".

*Primary Examiner*—Michael A. Brown
*Attorney, Agent, or Firm*—Oblon, Spivak, McClelland, Maier & Neustadt

[57] ABSTRACT

A hyperextension orthesis having a base plate, an abdominal rod extending downwards therefrom with a symphysis pad, branches extending to both sides with locking elements, and an upwardly extending chest rod on which the sternal pad is movably arranged. The hyperextension orthesis also includes an oblong hole provided in the chest rod, with a screw extending through the hole and connected to the sternal pad such that the chest rod is slidable with respect to the sternal pad. A sleeve is also formed in the chest rod, with the sleeve receiving a tongue extending from a lower portion of the sternal pad.

7 Claims, 1 Drawing Sheet

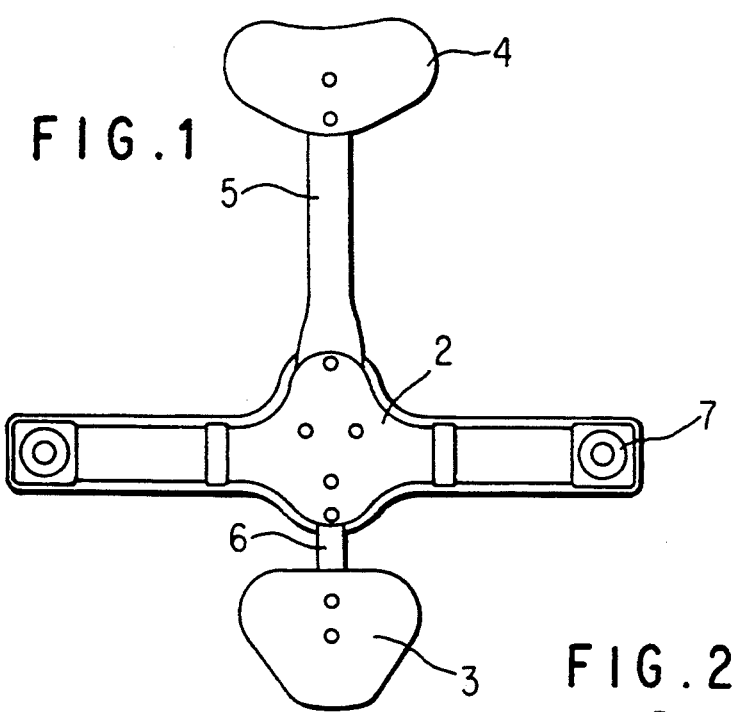
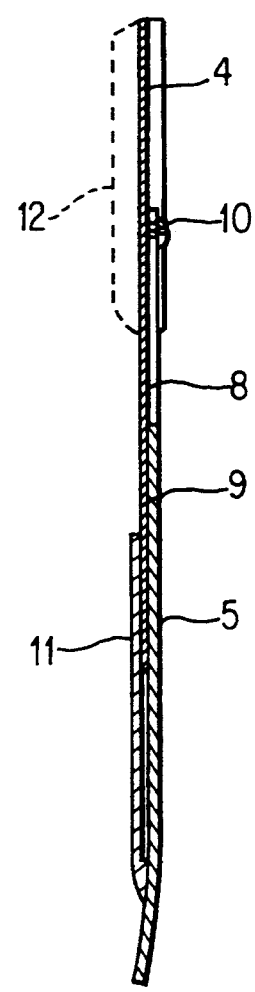
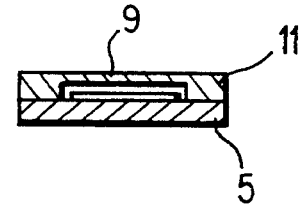
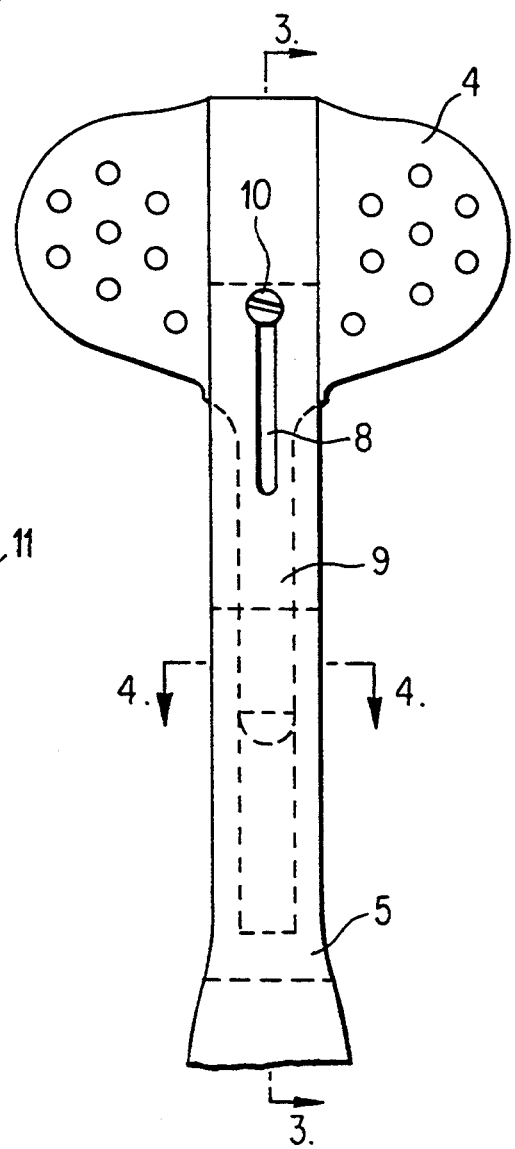
FIG.1
FIG.2
FIG.3
FIG.4

HYPEREXTENSION ORTHESIS WITH MOVABLE FRONT PAD

BACKGROUND OF THE INVENTION

Technical Field: The invention relates to an improved hyperextension orthesis, especially one in which the distance of the sternal pad from the base plate adapts automatically to different body postures during wearing.

In all known three-point support corsets after Bähler, so-called hyperextension ortheses, the pads are rigidly arranged. The distance of the pads from the base plate is adjusted by shortening the chest and abdominal rods upon adaptation by the orthopedic specialist. In the case of elderly patients there are difficulties, caused by incorrect posture and when sitting, to the extent that the sternal pad is pushed upwards as a result of the altered body posture and presses on the windpipe and leaves behind chafe marks.

The report by the company Otto Bock: "Hyperextensionsorthese in Modulbauweise" [Hyperextension orthesis in modular design] in Medizinisch-Orthopädische Technik, Volume 5, 1987 and Reissue U.S. Pat. No. 31,564 disclose hyperextension ortheses of the generic type which, with the aid of oblong holes, permit a simple adaptation of the position of sternal pad and symphysis pad to the body size of the patient. However, only one single adaptation is possible in this way. The real problem of a dynamic adaptation of the position of the sternal pad to the respective body posture of the patient is consequently not solved.

SUMMARY OF THE INVENTION

The aim of the present invention is therefore to provide a constructional design of a hyperextension orthesis which overcomes these disadvantages and which also ensures the correct positioning of the sternal pad in the event of a varying body posture of the wearer.

This objective is achieved by means of a hyperextension orthesis with a base plate, an abdominal rod extending downwards therefrom with a symphysis pad, branches extending to both sides with locking elements, and an upwardly extending chest rod at whose end an oblong hole is provided for engagement of a screw for securing a sternal pad. The characterizing feature of the construction according to the invention consists in the fact that the sternal pad has a groove for receiving the chest rod, and an elongate tongue extending out from the lower end of the pad for movable engagement in a slide sleeve formed in [sic] on the chest rod at a distance from the oblong hole.

The screw for securing the sternal pad is chosen in such a way that the screw head bears securely only on the chest rod, so that a sliding in the oblong hole is readily possible.

The groove for receiving the chest rod is preferably formed on the side of the sternal pad directed away from the body, and the slide sleeve is preferably arranged on the side of the chest rod directed toward the body. Upon initial adjustment of the hyperextension orthesis, the length of the chest rod is chosen such that the hyperextension orthesis bears upon the correct body site. If the distance between the sternal pad and the base plate is now shortened as a result of a change of body posture, the tongue or the slide pushes deeper into the slide sleeve of the chest rod, as a result of the secure positioning of the sternal pad on the body, so that the upward pushing of the sternal pad and the pressure on the windpipe do not occur. If the body posture leads to an increased distance between the sternal pad and the base plate, the slide slips slightly further out of the slide sleeve. This constructional design of a movable slide adapts the distance between sternal pad and base plate automatically to the body posture, the pressure of the sternal pad upon the body remaining basically constant. The relief of the vertebral bodies of the lumbar spine and thoracic spine achieved by the corset is likewise maintained constant.

The slide sleeve can be made of plastic or metal. Suitable plastics are thermo plastics with good surface properties, such as polyamide, polyolefins, polyurethanes, polycarbonate. Homopolymers are suitable as well as copolymers.

The slide sleeve preferably has a U-shaped cross-section, so that between the chest rod and the slide sleeve there is a space for receiving the tongue.

If the slide sleeve is made of plastic, it can be connected to the chest rod by means of gluing, riveting or screwing. If the slide sleeve is made of metal, it can be connected to the chest rod by means of gluing, riveting, soldering or welding. The slide sleeve can also be worked out from the material of the chest rod itself, if the material is chosen appropriately thick. In order to produce a slidable connection between the tongue and the chest rod, in another embodiment, in order to form a slide sleeve, the chest rod is bent round to such an extent that the bent edges cover over the tongue 9 at least partially. In such an embodiment it is preferable for the gap which may remain between the bent edges of the chest rod to be covered with a plastic film. If the tongue and the chest rod are made of metal, it is preferable for the surface of the slide sleeve and/or the tongue and the chest rod to be provided with a plastic layer with good surface slip. A plastic which is particularly preferred for this purpose is polytetrafluoroethylene. However, other plastics can also be used for the surface coating.

The chest rod is normally made of metal. It is also possible, in principle, to form the chest rod from fiber-reinforced plastic. In this case it is advantageous, for reasons of production technology, to form the slide sleeve simultaneously, for example by injection molding.

BRIEF DESCRIPTION OF THE DRAWINGS

The invention is illustrated in greater detail with reference to the Figures in which:

FIG. 1 is a front view of a hyperextension orthesis;

FIG. 2 is a partial view of a hyperextension orthesis in accordance with the present invention depicting the connection of the sternal pad and chest rod;

FIG. 3 is a side, cross-sectional view along line A-B of FIG. 2; and

FIG. 4 is a cross-sectional view along line C-D of FIG. 2.

DETAILED DESCRIPTION OF THE PREFERRED EMBODIMENT

FIG. 1 shows the front part of a hyperextension orthesis in a diagrammatic representation. Reference number 2 designates the base plate, from which there downwardly extends the abdominal rod 6 at whose end the symphysis pad 3 is secured. Extending upwards from the base plate 2 is the chest rod 5, with the sternal pad 4 arranged at its end. Extending to each side from the base plate 2 are branches at whose respective ends locking elements 7 are provided for connection to the back part (not shown).

FIG. 2 shows the design according to the invention of the chest rod 5 and of the sternal pad 4. On the surface of the sternal pad 4 directed away from the body there is a groove for receiving the chest rod 5. The chest rod has at its end an oblong hole 8 extending in the longitudinal direction. The oval sternal pad 4 has at its lower end an elongate tongue as a slide for engagement in the slide sleeve 11, which is guided between the sleeve and the chest rod 5.

The connection of the sternal pad 4 to the chest rod 5 is effected by the screw 10 which is screwed into the pad through the oblong hole 8 in the chest rod 5. The screw head can slide in the oblong hole 8 on the chest rod 5, at the same time as which the depth of insertion of the tongue 9 into the slide sleeve 11 in the chest rod alters.

FIG. 3 is a section along the line A-B in FIG. 2 and shows the design of the guide for the tongue 9, which is designed as slide sleeve 11. The sternal pad 4 with the slide 9 is connected in a slidable manner to the chest rod 5 by means of this constructional design. The slide 9 pushes into the gap between the slide sleeve 11 and the chest rod 5 and is secured against complete pulling out from the screw 10, which can slide in the oblong hole 8 of the chest rod. It is preferable to provide the side of the sternal pad 4 directed toward the body with a padding 12. It has proven particularly advantageous to design the padding 12 with a wedge-shaped cross-section, i.e. thicker at the upper end of the pad 4 than at the lower end.

FIG. 4 is a section along the line C-D in FIG. 2 and shows an embodiment of the slide sleeve 11 on the chest rod 5, with the slide 9 guided therein. A U-shaped part 11 is arranged on the side of the chest rod 5 directed toward the body in such a way that the slide 9 can be pushed into the slot between the chest rod and the legs of the U-profile. However, it is also possible, in principle, for the edges of the chest rod 5 to be bent round to such an extent that they engage over the slide, in order to form a slide guide. In such an embodiment it is advantageous to cover the guide completely with a protective layer in order to prevent the catching of foreign bodies in the guide rail. The chest rod 5 and slide 9 are made of stable material, preferably of metal. However, it is also possible, in principle, to produce the sternal pad with a slide made of fiber-reinforced plastic. In order to obtain a permanent, low-noise sliding, it is advantageous to cover the slide 9 or the surface of the chest rod 10 [sic] and the slide sleeve 11 with a plastic with good surface slip. It is particularly advantageous to produce the U-shaped part 11 itself from a plastic with good surface slip.

The secure connection of the slide sleeve 11 to the chest rod 5 can be achieved, for example, by gluing, riveting, screwing or soldering.

However, it is also possible, in principle, to arrange the guide for the slide 9 on the side of the chest rod 5 directed away from the body. However, this design is not preferred since the slide sleeve 11 must then be made more stable in order to guarantee the necessary support guiding of the chest rod 5 for the sternal pad 4.

I claim:

1. A hyperextension orthesis comprising:
a sternal pad;
a base plate, an abdominal rod extending downwards therefrom with a symphysis pad, branches extending to both sides with locking elements, and an upwardly extending chest rod at whose end an oblong hole is provided for engagement of a screw for securing the sternal pad, said hyperextension orthesis further including a slide sleeve formed on said chest rod;
wherein the sternal pad has a groove for receiving the chest rod and an elongate tongue extending out from a lower end of the sternal pad, for movable engagement in said slide sleeve formed on the chest rod at a distance from the oblong hole.

2. The hyperextension orthesis according to claim 1, wherein the groove for receiving the chest rod is arranged on the side of the sternal pad directed away from the body, and the slide sleeve is arranged on the side of the chest rod directed toward the body.

3. The hyperextension orthesis according to claim 1, wherein the slide sleeve has a U-shaped cross-section.

4. The hyperextension orthesis according to claim 3, wherein the slide sleeve is made of plastic or metal.

5. The hyperextension orthesis according to claim 1, wherein, in order to form a slide sleeve, the slide edge of the chest rod is bent round to such an extent that the bent edges cover over the tongue at least partially.

6. The hyperextension orthesis according to claim 1, wherein at least one of the tongue is provided with a plastic layer having good surface slip.

7. A hyperextension orthesis comprising:
a base plate;
an upwardly extending chest rod having an upper portion with an oblong hole provided therein;
a sternal pad having a groove therein for receiving said upper portion of said chest rod, and wherein a screw extends through said oblong hole and into said sternal pad such that said chest rod is movable with respect to said sternal pad;
wherein said chest rod further includes a sleeve defining a passage extending along a lengthwise direction of said chest rod, said sleeve spaced from said oblong hole, said sternal pad further including a tongue extending from a lower end thereof, said tongue extending into said sleeve.

* * * * *

UNITED STATES PATENT AND TRADEMARK OFFICE
CERTIFICATE OF CORRECTION

PATENT NO. : 5,342,289
DATED : August 30, 1994
INVENTOR(S) : Kurt MUNNY

It is certified that error appears in the above-indentified patent and that said Letters Patent is hereby corrected as shown below:

Column 3, line 30, change "toward" to --away--.

Column 4, line 10, change "I claim:" to --What is claimed as new and desired to be secured by Letters Patent of the United States:--.

Column 4, line 40, before "tongue" insert --inner surface of the slide sleeve and the surface of the--.

Signed and Sealed this

Twenty-second Day of October, 1996

Attest:

BRUCE LEHMAN

Attesting Officer

Commissioner of Patents and Trademarks